(12) United States Patent
Naka

(10) Patent No.: US 8,907,544 B2
(45) Date of Patent: Dec. 9, 2014

(54) ULTRASONIC TRANSDUCER

(71) Applicant: Nihon Dempa Kogyo Co., Ltd., Tokyo (JP)

(72) Inventor: Yoji Naka, Saitama (JP)

(73) Assignee: Nihon Dempa Kogyo Co., Ltd., Tokyo (JP)

( * ) Notice: Subject to any disclaimer, the term of this patent is extended or adjusted under 35 U.S.C. 154(b) by 142 days.

(21) Appl. No.: 13/761,162

(22) Filed: Feb. 7, 2013

(65) Prior Publication Data

US 2013/0207517 A1 Aug. 15, 2013

(30) Foreign Application Priority Data

Feb. 15, 2012 (JP) ................................. 2012-030097

(51) Int. Cl.
*B06B 1/06* (2006.01)
*H01L 41/053* (2006.01)
*G01N 29/24* (2006.01)

(52) U.S. Cl.
CPC ............ *H01L 41/0533* (2013.01); *G01N 29/24* (2013.01)
USPC ....................................................... 310/334

(58) Field of Classification Search
CPC ...... H01L 41/053; B06B 1/06; B06B 1/0644; B06B 1/0688
USPC .......................................... 310/322, 334, 335
See application file for complete search history.

(56) References Cited

U.S. PATENT DOCUMENTS

2008/0116765 A1 * 5/2008 Sugiura et al. ................. 310/334

FOREIGN PATENT DOCUMENTS

| JP | 06-085775 | 3/1994 |
|---|---|---|
| JP | 2006-068194 | 3/2006 |
| JP | 2007-267817 | 10/2007 |
| JP | 2007-530207 | 11/2007 |
| JP | 2009-195305 | 9/2009 |
| JP | 4584321 | 11/2010 |
| JP | 2011-067262 | 4/2011 |

* cited by examiner

*Primary Examiner* — Derek Rosenau
(74) *Attorney, Agent, or Firm* — Jianq Chyun IP Office

(57) ABSTRACT

An ultrasonic transducer includes an ultrasonic transmitting and receiving portion, a housing, a driving device, a casing, a first volume compensation mechanism, a ventilating portion, a diaphragm, and a component. The housing houses the ultrasonic transmitting and receiving portion, and the housing seals ultrasonic propagation liquid. The driving device is configured to drive the ultrasonic transmitting and receiving portion. The casing houses the driving device. The first volume compensation mechanism is configured to absorb a volume change of the ultrasonic propagation liquid. The diaphragm divides an internal space of the casing into at least a first internal space and a second internal space. The ventilating portion is configured to ventilate the first internal space to outside of the casing. The component is disposed in a space other than the first internal space in the internal space and includes a frame ground that electrically connects to an electrical circuit.

8 Claims, 8 Drawing Sheets

ULTRASONIC TRANSDUCER

CROSS REFERENCE TO RELATED APPLICATIONS

This application claims the priority benefit of Japan application serial no. 2012-030097, filed on Feb. 15, 2012. The entirety of the above-mentioned patent application is hereby incorporated by reference herein and made a part of this specification.

TECHNICAL FIELD

This disclosure relates to a short axis mechanical scan type ultrasonic transducer where an ultrasonic transmitting and receiving portion is mechanically reciprocated in the short axis direction and the linear direction to perform ultrasonic diagnostics of a test object. Especially, this disclosure relates to an ultrasonic transducer that prevents entrance of air in ultrasonic propagation liquid and prevents deformation of a portion of a housing contacting the test object due to change in internal pressure caused by temperature change of the ultrasonic propagation liquid in the housing where the ultrasonic transducer is housed.

DESCRIPTION OF THE RELATED ART

A short axis mechanical scan type ultrasonic transducer, as illustrated in FIG. 5, for example, electronically scans an ultrasonic transmitting and receiving portion in the long axis direction. The short axis mechanical scan type ultrasonic transducer also mechanically scans the ultrasonic transmitting and receiving portion 15 in the short axis direction with a timing belt movement mechanism 16 and a linear guide 17. This obtains a three-dimensional image of a test object (a living body). Then, for ensuring good propagation of ultrasonic, ultrasonic propagation liquid such as oil, is sealed in a housing 18 of the ultrasonic transducer (Japanese Patent No. 4584321).

The ultrasonic transducer, which seals this ultrasonic propagation liquid in the housing, causes change in the volume of the sealed liquid by temperature change. Therefore, the following failures may occur.

That is, first, in the case where a temperature of usage environment is high, the sealed propagation liquid is expanded, causing rising of the internal pressure in the housing. Then, the sealed propagation liquid may leak from a joint portion of each component that seals the propagation liquid in the housing to outside of the housing. On the other hand, in the case where the temperature of usage environment is low, the propagation liquid in the housing contracts, lowering the internal pressure in the housing. This may cause mix of air in the propagation liquid sealed in the housing from an oil seal portion, which is formed at a driving force transmission mechanism that drives the ultrasonic transmitting and receiving portion for sealing. Further, in the case where the temperature of usage environment becomes low after the liquid sealed at a high temperature leaks outside of the housing, the possibility of entering air into the propagation liquid increases. The air mixed into the propagation liquid becomes an air bubble, adversely affecting an ultrasonic image obtained by an ultrasonic diagnostics.

In the case where the surface area of the housing of the ultrasonic transducer is large, especially, in the case where the surface of the housing in contact with a body surface of a subject is approximately flat, the deformation of the contact surface of the housing due to change in the volume of the above-described propagation liquid is remarkable. This changes a distance (a gap) between the flat portion of the ultrasonic transmitting and receiving portion and the inner surface (the inner wall) of the housing of the ultrasonic transducer, and causes instability of the ultrasonic image obtained by the ultrasonic diagnostics, resulting in a failure in diagnosis.

Therefore, the conventional ultrasonic transducer of this type employs a constitution illustrated in FIG. 6A so as not to prevent working of a volume compensation mechanism of an ultrasonic propagation medium, sealed in the housing. In this constitution, an air hole 21a is disposed on the bottom portion of a casing 21, and an air film 20, which transmits only a gas, is provided. As illustrated in FIG. 6B, some conventional ultrasonic transducers include an air pipe 23 inside of a tube 22. The reference numeral 24 indicates a driving device of ultrasonic transmitting and receiving apparatus.

As illustrated in FIG. 7, in the conventional intracavitary diagnostic system, a structure where a member surrounded by a first sterilization sheet 33 is separated by a stretchable second sterilization sheet 30 has been proposed. The second sterilization sheet 30 separates a contaminated zone 32 of a driving portion 27 and a clean zone 31 of a holder 29 of a catheter 28.

As illustrated in FIG. 8, the conventional ultrasonic probe includes different diaphragms 41 and 42 in a liquid chamber 40, which houses ultrasonic propagation liquid for the ultrasonic probe. The ultrasonic probe that includes respective oil seals 43 and 44 to prevent air leakage has been proposed.

Additionally, as illustrated in FIG. 9, the conventional ultrasonic transducer forms an integrated space by connecting a hollow pressurization member 51 made of a rubber material to the inside of an acoustic window 52. In some of the conventional ultrasonic transducers, an appropriate amount of liquid-form acoustic propagation liquid is filled into the internal space to generate internal pressure by deformation of the pressurization member 51.

However, this type of ultrasonic transducer described above has problems that will be described below.

That is, in the volume compensation mechanism of the ultrasonic propagation liquid of the ultrasonic transducer illustrated in FIG. 6A, the air film 20 transmits humidity besides air. In use over a long period, the humidity gradually enters into a driving mechanism or similar of the transducer and may generate rust or similar in a metal component constituting the driving mechanism of the transducer. After humidity enters into the inside of the driving mechanism or similar, when a temperature in the casing 21 becomes low, condensation occurs on the inner surface of the casing 21. This causes insufficient electrical insulation between the inside and the outside of the casing 21, resulting in loss of safety for use of the ultrasonic transducer.

The structure illustrated in FIG. 7 only separates the contaminated zone 32 and the clean zone 31 with a stretchable second sterilization sheet 30 and does not divide the internal space of the casing. This cannot prevent entrance of a gas and humidity into the driving portion or similar.

Further, the structure illustrated in FIG. 8 does not suggest the direction of the oil seals 43 and 44 disposed at the diaphragms 41 and 42 in the liquid chamber 40.

Additionally, the structure illustrated in FIG. 9 simply suggests an example where a change in a volume of ultrasonic propagation liquid is absorbed using the pressurization member 51 made of rubber. This does not suggest that the internal space of the casing 52 is divided into a plurality of spaces, and a volume compensation mechanism is disposed in these spaces.

A need thus exists for an ultrasonic transducer which is not susceptible to the drawback mentioned above.

SUMMARY

According to an aspect of this disclosure, there is provided an ultrasonic transducer. The ultrasonic transducer includes an ultrasonic transmitting and receiving portion, a housing, a driving device, a casing, a first volume compensation mechanism, a ventilating portion, a diaphragm, and a component. The housing houses the ultrasonic transmitting and receiving portion inside of the housing. The housing seals an ultrasonic propagation liquid inside of the housing. The driving device is configured to drive the ultrasonic transmitting and receiving portion. The casing houses the driving device inside of the casing. The first volume compensation mechanism is configured to absorb a volume change of the ultrasonic propagation liquid. The diaphragm divides an internal space of the casing into at least a first internal space and a second internal space. The diaphragm prevents movement of a gas between the first internal space and another space in the internal space of the casing. The ventilating portion is configured to ventilate the first internal space to outside of the casing. The component is disposed in a space other than the first internal space in the internal space of the casing. The component includes a frame ground that electrically connects to an electrical circuit.

BRIEF DESCRIPTION OF THE DRAWINGS

The foregoing and additional features and characteristics of this disclosure will become more apparent from the following detailed description considered with the reference to the accompanying drawings, wherein:

FIG. 2A illustrates a state where ultrasonic propagation liquid does not flow into the volume compensation mechanism, and FIG. 2B illustrates a state where the ultrasonic propagation liquid flows into the first internal space and expands;

FIG. 3A is a partially enlarged cross-sectional view of the oil seal portion where one oil seal is disposed at an driving rotation shaft of an ultrasonic transmitting and receiving portion, and FIG. 3B is a partially enlarged cross-sectional view of the oil seal portion where two oil seals are serially disposed along the axial direction of the driving rotation shaft;

FIG. 6A is a conventional example where an air film, which passes through only a gas, is disposed on a base portion side of the casing, and FIG. 6B is a conventional example where a tube is disposed at the base portion of the casing and an air pipe is inserted through the tube.

DETAILED DESCRIPTION

A description will be given of an ultrasonic transducer according to embodiments of this disclosure based on the attached drawings.

Embodiment 1

Figure 1A:
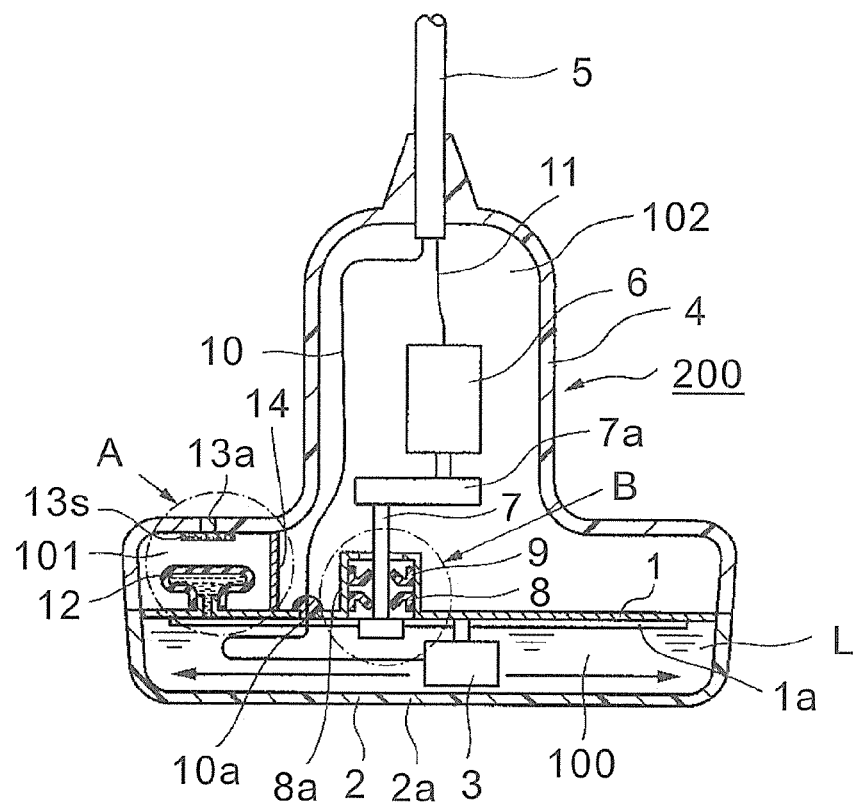
FIG. 1A is a vertical cross-sectional view of an ultrasonic transducer according to Embodiment 1 of this disclosure in the long axis direction.
Figure 1B:
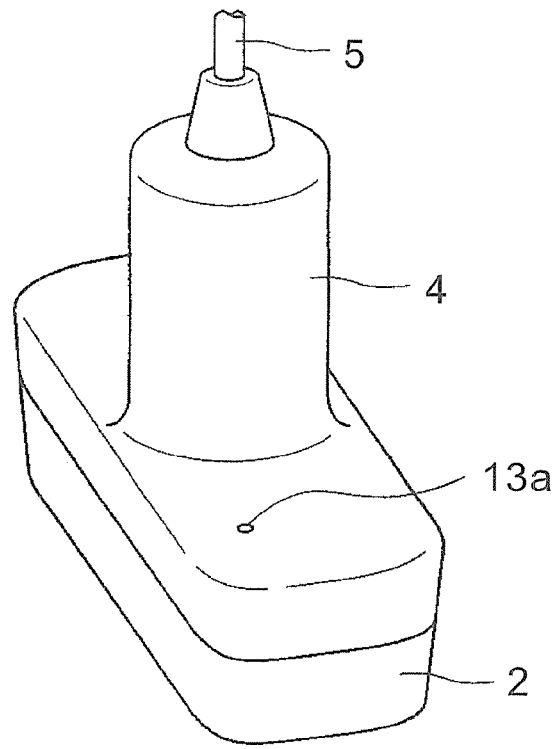
FIG. 1B is a perspective view of FIG. 1A viewed from the arrow A direction.

As illustrated in FIG. 1A, an ultrasonic transducer according to Embodiment 1 of this disclosure is an ultrasonic transducer 200, which includes a chassis 1, a shaft bearing portion 8a, an ultrasonic transmitting and receiving portion 3, a driving shaft 7, and a transducer driving portion. The chassis 1 is made of resin material. The shaft bearing portion 8a is vertically disposed on the top surface of the chassis 1 and integrally formed with the chassis 1. The ultrasonic transmitting and receiving portion 3 is pivotally supported to the shaft bearing portion 8a via two oil seals 8 and 9. The driving shaft 7 reciprocates the ultrasonic transmitting and receiving portion 3 along a linear guide 1a disposed on the bottom surface of the chassis 1 in the short axis direction. The transducer driving portion includes an ultrasonic transmitting and receiving portion driving device (a drive motor) 6. The ultrasonic transmitting and receiving portion driving device (the drive motor) 6 is fixedly secured to a bracket (not shown) on the top surface of the chassis 1 via a timing pulley 7a.

Figure 5:
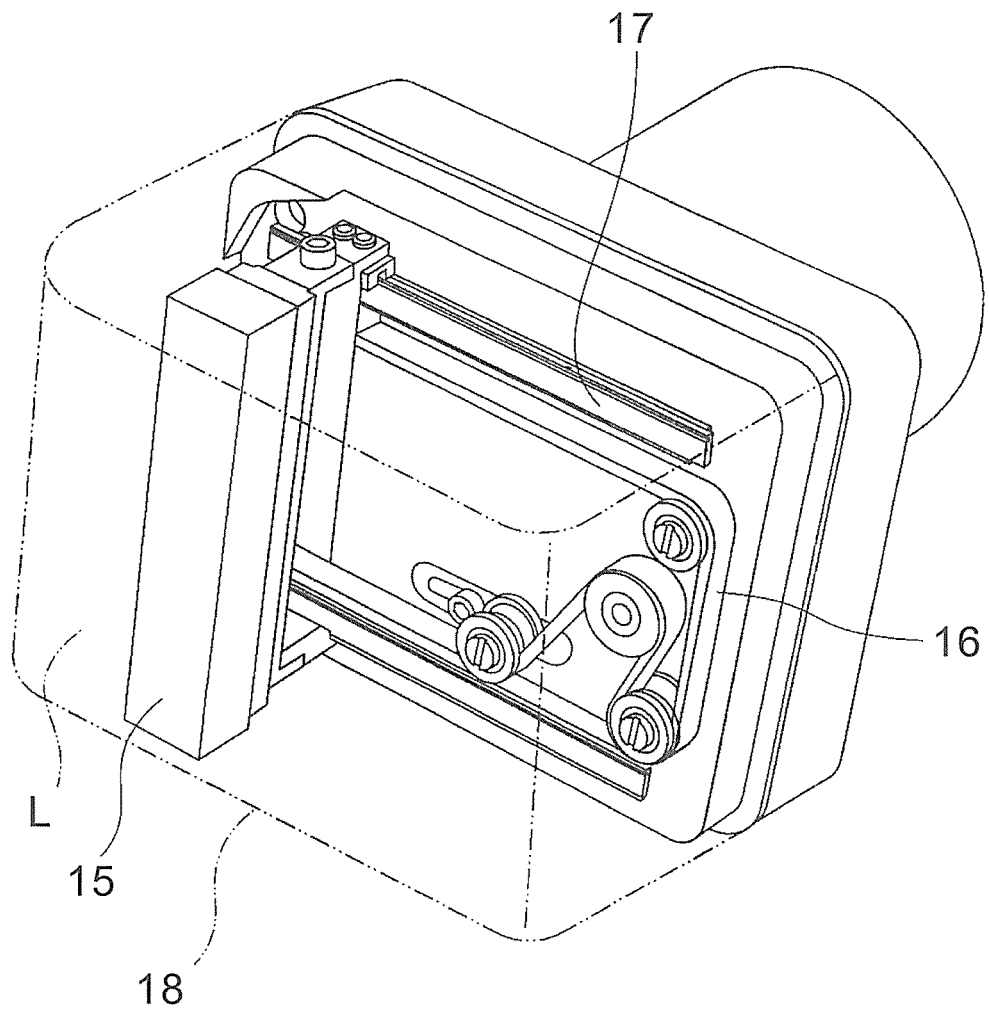
FIG. 5 is a perspective view of a movement mechanism, which reciprocates the ultrasonic transmitting and receiving portion of the conventional ultrasonic transducer in the short axis direction, where a housing is removed and viewed from the ultrasonic transmitting and receiving portion direction.
Figure 6A:
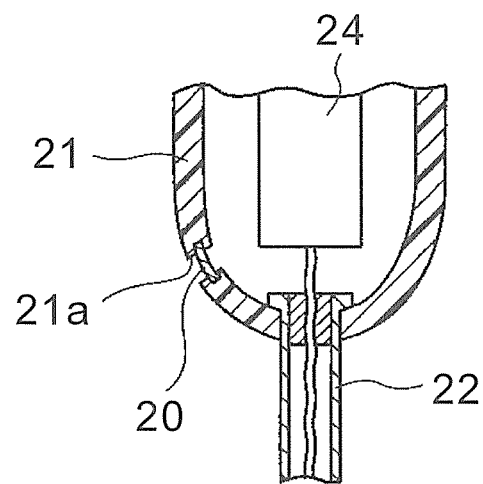
FIGS. 6A and 6B illustrate a volume compensation mechanism of the conventional ultrasonic transducer.
Figure 6B:
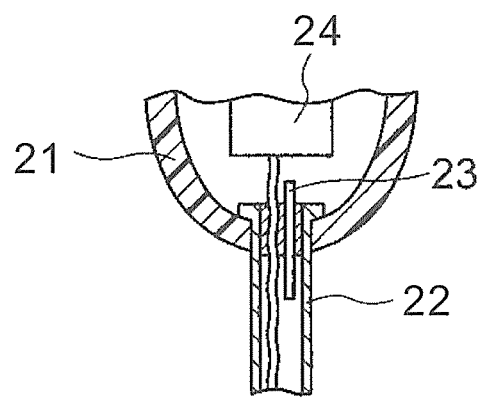
Figure 7:
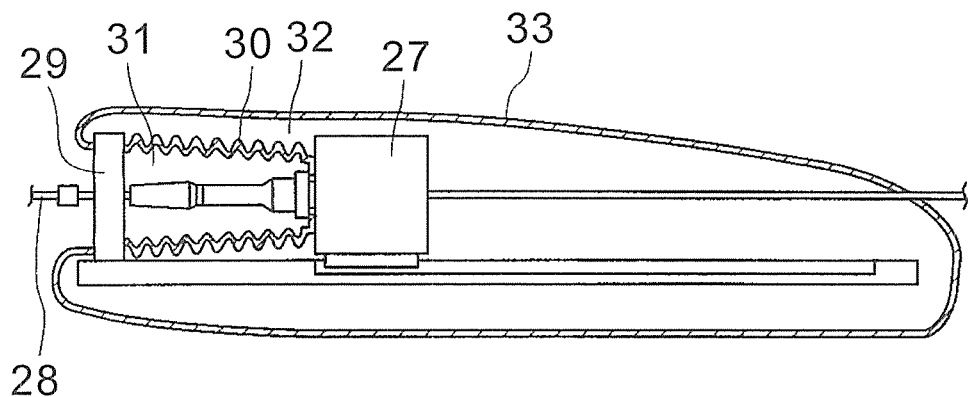
FIG. 7 illustrates a constitution of a conventional intracavitary diagnostic system where a stretchable sterilization sheet separates a contaminated zone of a driving portion from a clean zone of a catheter holder.
Figure 8:
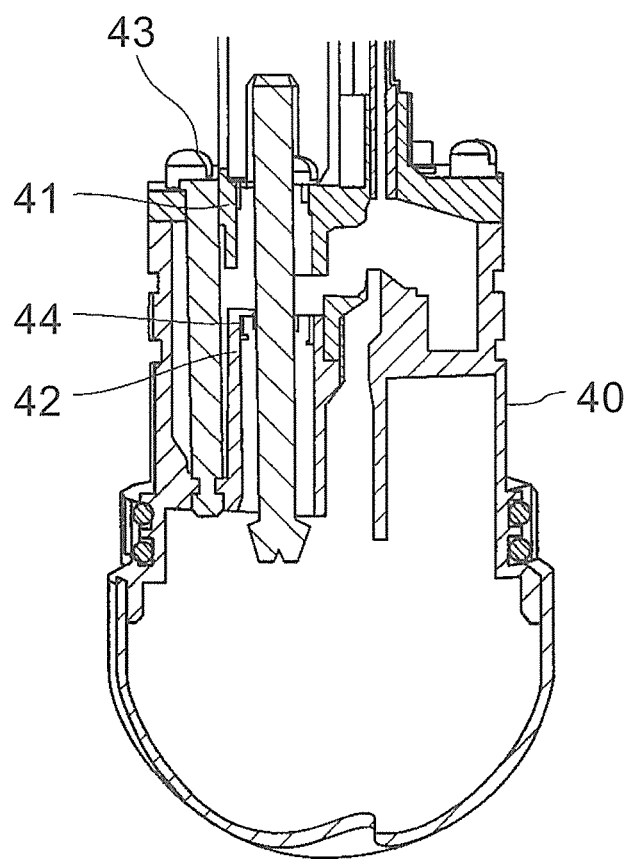
FIG. 8 is a conventional example of the conventional ultrasonic probe where respective oil seals are disposed at diaphragms, which separate a liquid chamber.
Figure 9:
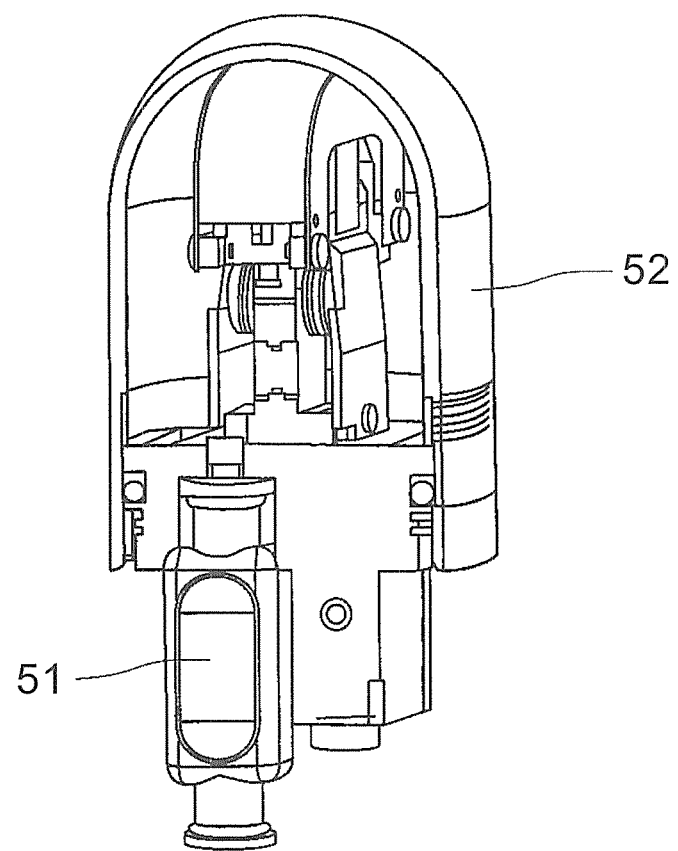
FIG. 9 is a conventional example of the conventional ultrasonic transducer where a pressurization member made of rubber absorbs a volume change of an ultrasonic propagation medium.

Here, as illustrated in FIG. 1A, a drive control cable 11, which is a part of a cable 5, is electrically connected to the drive motor 6. A current is supplied to the drive motor 6 such that the ultrasonic transmitting and receiving portion 3 can reciprocate in the short axis direction. Additionally, an ultrasonic signal cable 10, which is the other part of the cable 5, is inserted through a bush 10a disposed at the chassis 1 and electrically connects to the ultrasonic transmitting and receiving portion 3. This allows transmission of a pulse signal to a piezoelectric element group constituting the ultrasonic transmitting and receiving portion 3 and reception of an ultrasonic signal detected from a specimen (a subject). Further, the cover shield of the cable 5 electrically connects to a bracket made of metal, an exterior casing of the drive motor, and a shield member (not shown) or similar member as a frame ground. The conventional reciprocating mechanism illustrated in FIG. 5 is employed for reciprocation of the ultrasonic transmitting and receiving portion 3. A housing 2 made of synthetic resin fits, is secured to, and covers the bottom surface edge portion of the chassis 1. Then, a space is formed between the bottom surface of the chassis 1 and the inner wall portion of the housing 2. The space is employed as an ultrasonic propagation liquid chamber 100 that houses ultrasonic propagation liquid L, for example, oil. A flat portion 2a of the housing 2 contacts a body surface of the subject.

Especially, the ultrasonic transducer according to this disclosure includes the casing 4 in which an internal space is least divided into a first internal space 101 and a second internal space 102. The first internal space 101 and the second internal space 102 are mutually and fluidically isolated. A ventilating portion 13 is disposed at the first internal space 101. The ventilating portion 13 ventilates a first volume compensation mechanism 12 and the casing 4 to outside air atmosphere. Further, a diaphragm (a divider) 14 is disposed among the first internal space 101, the second internal space 102, and another internal space to prevent movement (flow) of a gas (air). For example, the diaphragm (the divider) 14 is vertically disposed between the top surface portion of the chassis 1 and the inner wall of the casing 4. The second internal space 102, which is completely fluidically isolated from the first internal space 101 and an ultrasonic propagation liquid chamber 100, houses an electric component, such as the above-described drive motor 6, the ultrasonic signal cable 10, the drive control cable 11, an electrical circuit, a frame ground connected via a bracket or similar, or similar member that is susceptible to rust, corrosion, or similar due to water vapor, humidity, or other causes.

Figure 2A:
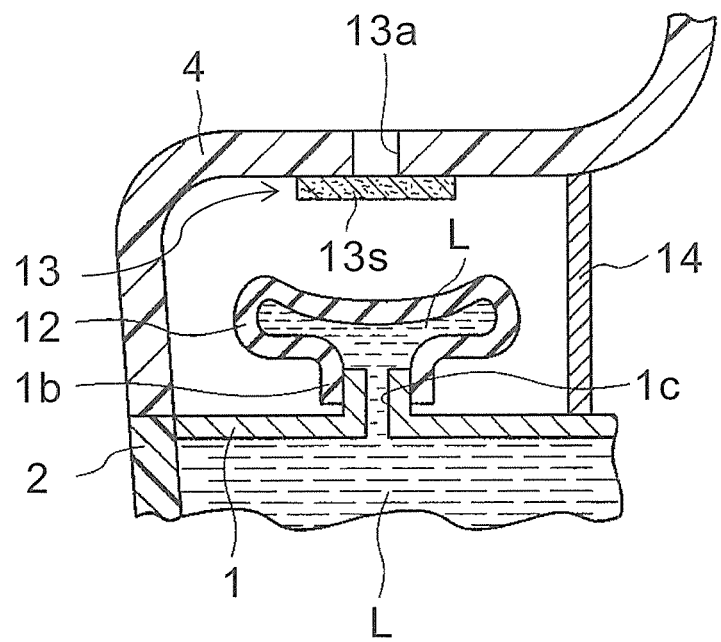
FIGS. 2A and 2B are partially enlarged cross-sectional views of a volume compensation mechanism, the volume compensation mechanism is disposed in a first internal space of an internal space, which is indicated by the arrow A in FIG. 1A, formed in a casing of the ultrasonic transducer according to this disclosure.
Figure 2B:
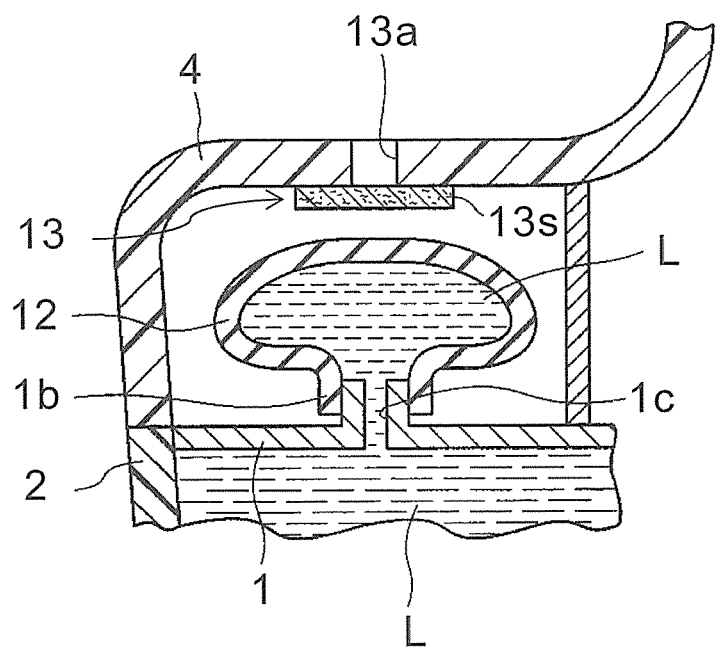

Especially, as illustrated in FIGS. 2A and 2B, the first volume compensation mechanism 12, which is housed in the first internal space 101, constituted of a saclike member formed of a flexible thin film where a cross-sectional shape is deformable. A projecting portion 1b, which is vertically disposed on the top surface portion of the chassis 1, includes a hole 1c. The first volume compensation mechanism 12 is mounted to the projecting portion 1b by fitting its neck portion of the saclike member into the projecting portion 1b. A breathable waterproof sheet 13s is fixedly secured to the inner wall of the casing 4. Only the gas in the first internal space 101 is discharged from an air hole 13a formed in the casing 4 through the waterproof sheet 13s to the atmosphere. Further, if water is sprinkled to the outer surface of the casing 4 when cleaning the ultrasonic transducer, the waterproof sheet 13s prevents the cleaning water or similar from entering into the first internal space 101 from the air hole 13a, which leads to external air. This prevents generation of mold, rust, or similar inside of the first internal space 101.

The first volume compensation mechanism 12 of the ultrasonic transducer according to this disclosure has the following structure. To reduce a pressure difference due to deformation of the first volume compensation mechanism 12 caused by a temperature change of the usage environment as much as possible, the flexible and deformable first volume compensation mechanism 12 is employed. The first volume compensation mechanism 12 employs a thin film with a thickness of, for example, approximately 0.05 mm to 1 mm to be formed into a sack. A material with high chemical resistance, such as PTFE (polytetrafluoroethylene) and polyvinylidene fluoride, is preferred as a material of this thin film. A material other than these may be selected depending on a material of the ultrasonic propagation liquid.

This is because, for example, in the case where a porous material, such as silicone rubber, is employed for the first volume compensation mechanism 12, a certain kind of liquid permeates and may cause a liquid leakage. The shape of the first volume compensation mechanism 12 is not limited to a saclike. A thin and long tube shape or a bellows-like shape may be applicable. In the case where the first volume compensation mechanism 12 has a bellows-like shape, this allows absorbing a larger volume change in the ultrasonic propagation liquid.

FIG. 1A illustrates a state where the first volume compensation mechanism 12 is under ordinary temperature and normal pressure and has a medium volume compared with the maximum volume. FIG. 2A illustrates a state where the volume of the ultrasonic propagation liquid becomes contracted due to such as falling of an ambient temperature at usage, causing contraction of the first volume compensation mechanism 12. FIG. 2B illustrates a state where the volume of the ultrasonic propagation liquid expands due to such as rising of the usage temperature, causing expansion of the first volume compensation mechanism 12.

With the constitution of the first volume compensation mechanism 12 according to the above-described disclosure, even if the usage temperature changes, the first volume compensation mechanism 12 disposed in the first internal space 101 is operated in atmospheric pressure. Accordingly, an internal pressure of the ultrasonic propagation liquid in the housing 2 is approximately equal to the atmospheric pressure, preventing deformation due to the internal pressure of the housing. Since the second internal space 102 is isolated from the external air by a diaphragm 14 or similar member, humidity does not enter into the second internal space 102. An electric component or similar member, which is disposed in the second internal space 102, does not rust. Moreover, this prevents safety of the ultrasonic transducer where such electrical insulation property is lost from degrading.

Further, the ultrasonic transducer according to Embodiment 1 of this disclosure seals the second internal space 102 as illustrated in FIG. 1A. With this structure, rising of the ambient temperature raises the internal pressure of the second internal space 102. This may cause a leakage of an air bubble from oil seals 8 and 9, which are disposed at a shaft bearing portion 8a, to the ultrasonic propagation liquid L in an ultrasonic propagation liquid chamber 100.

This leakage occurs by the following reason. Generally, an oil seal has a structure where a fluid is hard to be leaked to the outside (the atmosphere side) even if pressure on the fluid side becomes high. In contrast, in the case where the external (the atmosphere side) pressure becomes high, a gas tends to enter into a liquid side.

Figure 3A:
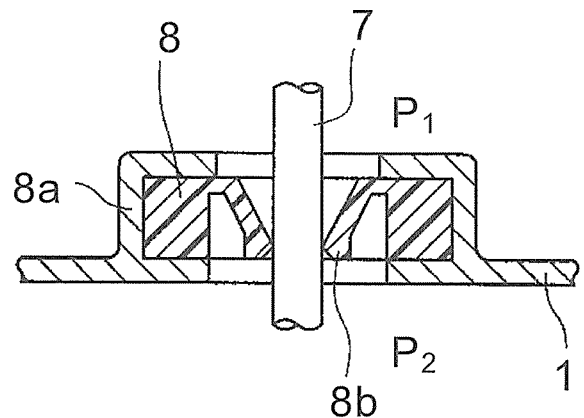
FIGS. 3A and 3B are partially enlarged cross-sectional views of an oil seal portion indicated by the arrow B in FIG. 1A.
Figure 3B:
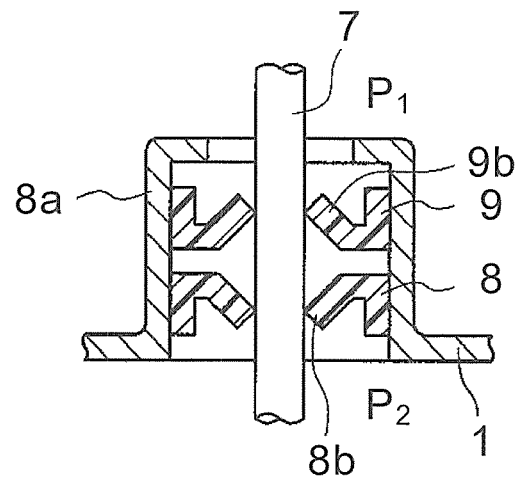

For example, the following describes the characteristic with an example where only one oil seal is disposed as illustrated in FIG. 3A. In the case where the relationship between the pressure at the gas side ($P_1$) and the pressure at the fluid side ($P_2$) is $P_1<P_2$, a rip 8b of the oil seal 8 faces the pressure $P_2$ direction. Then, the rip 8b is pressed against the driving shaft 7, and its sealing performance is easy to be maintained. In contrast, in the case where $P_2<P_1$ is met, a force is applied to the direction where the rip 8b is away from the driving shaft 7, and its sealing performance is hard to be maintained. Accordingly, as illustrated in FIG. 3B, one more oil seal 9 is serially added in the axial direction of the driving shaft 7 such that the rips 8b, 9b face in the reverse direction each other. Embodiment 1 according to this disclosure employs these two oil seals.

Embodiment 2

Figure 4:
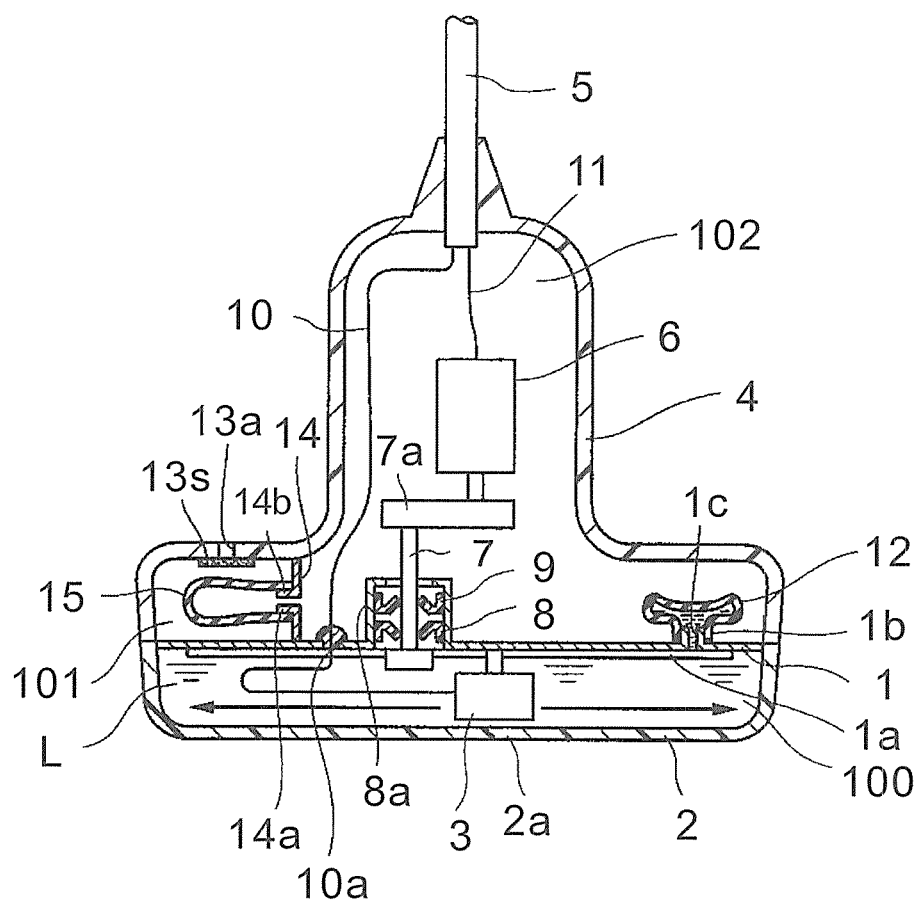
FIG. 4 is a vertical cross-sectional view of an ultrasonic transducer according to Embodiment 2 of this disclosure in the short axis direction.

As illustrated in FIG. 4, the ultrasonic transducer according to Embodiment 2 of this disclosure includes the above-described first volume compensation mechanism 12, a diaphragm (a divider) 14, and a second volume compensation mechanism 15. The first volume compensation mechanism 12 projects from the top surface of a chassis 1 in a second internal space 102. The diaphragm (the divider) 14 is disposed between a first internal space 101 and the second internal space 102. The second volume compensation mechanism 15 fluidically communicates with the second internal space 102 via a holes 14a, 14b in the diaphragm (the divider) 14 so as to make pressure in the second internal space 102 approximately equal to atmospheric pressure.

With this structure, when the temperature of the ambient environment of the ultrasonic transducer rises, ultrasonic propagation liquid L in an ultrasonic propagation liquid chamber 100 expands and the first volume compensation mechanism 12 is operated. The first volume compensation mechanism 12 is operated to push out the air in the second internal space 102 to the outside (in the atmosphere) by the expanded volume of the liquid. Thus, the respective internal pressures in the ultrasonic propagation liquid chamber 100 and the second internal space 102 are maintained approximately equal.

Meanwhile, air in the second internal space 102 also expands with rising of temperature. The air tries to flow out to the outside of the second internal space 102 by the volume where the expanded volume of the air is added to the expanded volume of the liquid. Here, the second volume compensation mechanism 15 is operated by the air by the volume of the summed expanded air, and is operated to push out the air by the changed volume to the first internal space 101. Thus, the respective internal pressures in the second internal space 102 and the first internal space 101 are maintained approximately equal.

At this time, the first internal space 101 leads to the external air and is maintained at atmospheric pressure; therefore, internal pressure of the second internal space 102 and the ultrasonic propagation liquid L in the ultrasonic propagation liquid chamber 100 are approximately equal to the atmospheric pressure. Although outside humidity might enter into the first internal space 101, the gas (the air) in the second internal space 102 is isolated from the gas in the first internal space 101 with the second volume compensation mechanism 15. This prevents outside humidity from entering into the second internal space 102.

This eliminates the possibility of generation of rust or similar on an electric component such as a motor and a circuit wiring, which are disposed in the second internal space 102, a frame ground, or similar member. This also eliminates the possibility of causing a problem such as degradation of safety due to a failure of electrical insulation.

With the ultrasonic transducer according to Embodiment 2 of this disclosure, respective internal pressures of the second internal space 102 and the ultrasonic propagation liquid L are approximately equal. This eliminates the need for additional oil seal, thus eliminating the need for increasing a drive load of a driving device.

The ultrasonic transducer according to this disclosure may form a third internal space, in addition to the second internal space 102, in a space in the casing 4 for a desired purpose.

According to an aspect of this disclosure, there is provided an ultrasonic transducer. The ultrasonic transducer includes an ultrasonic transmitting and receiving portion, a housing, a driving device, a casing, a first volume compensation mechanism, a ventilating portion, a diaphragm, and a component. The housing houses the ultrasonic transmitting and receiving portion inside of the housing. The housing seals ultrasonic propagation liquid inside of the housing. The driving device is configured to drive the ultrasonic transmitting and receiving portion. The casing houses the driving device inside of the casing. The first volume compensation mechanism is configured to absorb a volume change of the ultrasonic propagation liquid. The diaphragm divides an internal space of the casing into at least a first internal space and a second internal space, and the diaphragm prevents movement of a gas between the first internal space and another space in the internal space of the casing. The ventilating portion is configured to ventilate the first internal space to outside of the casing. The component is disposed in an internal space other than the first internal space. The component constitutes a part of an electrical circuit including a frame ground.

The ultrasonic transducer according to this disclosure may include the ventilating portion that is configured to allow a gas to pass and prevent a liquid from passing through the ventilating portion.

The ultrasonic transducer according to this disclosure may include the first volume compensation mechanism that is disposed in the first internal space.

The ultrasonic transducer according to this disclosure may further include a driving shaft and two oil seals. The driving shaft is configured to transmit power to the ultrasonic transmitting and receiving portion from the second internal space. The ultrasonic transmitting and receiving portion is in the housing which seals the ultrasonic propagation liquid. The two oil seals have a direction for pressure resistance on the driving shaft which transmits a power to the ultrasonic transmitting and receiving portion. The oil seals are serially disposed in opposite directions one another.

The ultrasonic transducer according to this disclosure may include the first volume compensation mechanism disposed in the second internal space. The second volume compensation mechanism is disposed at a diaphragm between the second internal space and the first internal space. In the case where a gas volume in the second internal space changes, the change in gas volume is absorbed and/or mitigated.

The ultrasonic transducer according to this disclosure may include the first and the second volume compensation mechanisms formed by a flexible and deformable thin film.

The ultrasonic transducer according to this disclosure may include the housing that includes a portion in contact with a body surface of a subject, the portion is a flat surface.

This disclosure prevents the ultrasonic propagation liquid from leaking outside, a gas from mixing into the propagation liquid, the surface of the housing contacting a test object from deforming, outside humidity from getting in the casing, and electrical safety from being lost due to condensation.

The principles, preferred embodiment and mode of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:
1. An ultrasonic transducer, comprising:
an ultrasonic transmitting and receiving portion;
a housing that houses the ultrasonic transmitting and receiving portion inside of the housing, the housing sealing an ultrasonic propagation liquid inside of the housing;
a driving device configured to drive the ultrasonic transmitting and receiving portion;
a casing that houses the driving device inside of the casing;
a first volume compensation mechanism configured to absorb a volume change of the ultrasonic propagation liquid;
a diaphragm that divides an internal space of the casing into at least a first internal space and a second internal space and prevents movement of a gas between the first internal space and another space in the internal space of the casing;

a ventilating portion configured to ventilate the first internal space to outside of the casing; and a component disposed in a space other than the first internal space in the internal space of the casing, the component including a frame ground that electrically connects to an electrical circuit.

2. The ultrasonic transducer according to claim 1, wherein the ventilating portion is configured to allow a gas to pass and prevent a liquid from passing through the ventilating portion.

3. The ultrasonic transducer according to claim 1, wherein the first volume compensation mechanism is disposed in the first internal space.

4. The ultrasonic transducer according to claim 1, further comprising:

a driving shaft configured to transmit a power to the ultrasonic transmitting and receiving portion from the second internal space, the ultrasonic transmitting and receiving portion being in the housing which seals the ultrasonic propagation liquid; and two oil seals having a direction for pressure resistance on the driving shaft, the oil seals being serially disposed in opposite directions one another.

5. The ultrasonic transducer according to claim 1, wherein the first volume compensation mechanism is disposed in the second internal space, wherein the ultrasonic transducer, further comprising:

a second volume compensation mechanism disposed at the diaphragm between the second internal space and the first internal space, wherein the second volume compensation mechanism configured to absorb a change in a gas volume in a case where the gas volume in the second internal space changes.

6. The ultrasonic transducer according to claim 1, wherein the first volume compensation mechanism is formed by a flexible and deformable thin film.

7. The ultrasonic transducer according to claim 5, wherein the first volume compensation mechanism and the second volume compensation mechanism are formed by a flexible and deformable thin film.

8. The ultrasonic transducer according to claim 1, wherein the housing includes a portion in contact with a body surface of a subject, the portion being a flat surface.

* * * * *